United States Patent [19]
Ascione et al.

[11] Patent Number: 5,968,481
[45] Date of Patent: Oct. 19, 1999

[54] PHOTOPROTECTIVE/COSMETIC COMPOSITIONS COMPRISING SYNERGISTIC ADMIXTURE OF SUNSCREEN COMPOUNDS

[75] Inventors: Jean-Marc Ascione, Paris; Delphine Allard, Colombes, both of France

[73] Assignee: Société L'Oréal S.A., Paris, France

[21] Appl. No.: 08/463,507

[22] Filed: Jun. 5, 1995

[30] Foreign Application Priority Data

Jun. 3, 1994 [FR] France ................................. 94 06828

[51] Int. Cl.$^6$ ................................ A61K 7/42; A61K 7/00
[52] U.S. Cl. ........................... 424/59; 424/60; 424/400; 424/401; 514/844; 514/938
[58] Field of Search ................... 424/59, 60, 400, 424/401; 514/844, 938

[56] References Cited

FOREIGN PATENT DOCUMENTS 0457687 11/1991 European Pat. Off. .
0518772 12/1992 European Pat. Off. .

*Primary Examiner*—Shelley A. Dodson
*Attorney, Agent, or Firm*—Burns, Doane, Swecker & Mathis, L.L.P.

[57] ABSTRACT

Topically applicable sunscreen/cosmetic compositions well suited for enhanced photoprotection of human skin and/or hair against the damaging effects of UV-A and UV-B irradiation, particularly solar radiation, comprise a photoprotecting synergistically effective amount of (i) 2,4,6-tris [p-((2'-ethylhexyl)oxycarbonyl)anilino]-1,3,5-triazine and (ii) 2-ethylhexyl α-cyano-β,β-diphenylacrylate, in a cosmetically acceptable vehicle, diluent or carrier therefor.

21 Claims, No Drawings

PHOTOPROTECTIVE/COSMETIC COMPOSITIONS COMPRISING SYNERGISTIC ADMIXTURE OF SUNSCREEN COMPOUNDS

CROSS-REFERENCE TO COMPANION APPLICATIONS

Copending applications
  Ser. No. 08/463,221, U.S. Pat. No. 5,607,664,
  Ser. No. 08/463,505, U.S. Pat. No. 5,605,678,
  Ser. No. 08/463,503, U.S. Pat. No. 5,489,431,
  Ser. No. 08/463,762, U.S. Pat. No. 5,605,679,
  Ser. No. 08/463,304, U.S. Pat. No. 5,658,555,
  Ser. No. 08/463,508, pending,
  Ser. No. 08/461,015, U.S. Pat. No. 5,667,765,
  Ser. No. 08/464,940, U.S. Pat. No. 5,609,853,
each filed concurrently herewith and each assigned to the assignee hereof.

BACKGROUND OF THE INVENTION

1. Technical Field of the Invention

The present invention relates to novel cosmetic compositions for topical application, for the photoprotection of the skin and/or the hair against ultraviolet radiation (such compositions hereinafter simply designated "sunscreen," "sunscreen/cosmetic" or "photoprotective/sunscreen" compositions), and to the use of same for the cosmetic applications indicated above.

This invention more especially relates to the aforesaid sunscreen/cosmetic compositions comprising, in a cosmetically acceptable vehicle, carrier or diluent, combinatory immixture of at least two particular and unique sunscreen compounds, namely, on the one hand, 2,4,6-tris[p-((2'-ethylhexyl)oxycarbonyl)anilino]-1,3,5-triazine and, on the other, 2-ethylhexyl α-cyano-β,β-diphenylacrylate. This admixture imparts enhanced solar protection factors to the subject compositions via an unexpected synergistic effect.

2. Description of the Prior Art

It is well known to this art that light radiation of wavelengths of from 280 nm to 400 nm promotes tanning of the human epidermis, and that irradiation of wavelengths of from 280 to 320 nm, i.e., UV-B irradiation, causes erythema and burning of the skin which can impair the development of a natural tan; hence, such UV-B radiation must thus be screened from the skin.

It is also known to this art that UV-A radiation, of wavelengths from 320 to 400 nm, which tans the skin, also adversely affects it, in particular in the event of sensitive skin or a skin which is continually exposed to solar radiation.

UV-A rays cause, in particular, a loss in the elasticity of the skin and the appearance of wrinkles, promoting a premature aging thereof. Such irradiation promotes triggering of the erythematous reaction or enhances this reaction in certain individuals, and may even be the source of phototoxic or photoallergic reactions. Thus, it is desirable to also screen out UV-A radiation.

A wide variety of cosmetic compositions intended for the photoprotection (UV-A and/or UV-B) of human skin are known to this art.

These photoprotective/sunscreen compositions are typically oil-in-water emulsions (namely, a cosmetically acceptable vehicle, carrier or diluent comprising an aqueous continuous dispersing phase and an oily discontinuous dispersed phase) which contains, in various concentrations, one or more standard lipophilic and/or hydrophilic organic sunscreen compounds capable of selectively absorbing harmful or deleterious UV radiation. These sunscreen compounds (and the amounts thereof) are selected as a function of the desired sun protection factor (the sun protection factor (SPF) being expressed mathematically by the ratio of the irradiation time required to attain the erythema-forming threshold with the UV screening agent to the time required to attain the erythema-forming threshold in the absence of UV screening agent).

SUMMARY OF THE INVENTION

It has now unexpectedly and surprisingly been determined that a unique combination of two particular sunscreen compounds provides photoprotective/sunscreen compositions having protection factors which are markedly improved, and in all instances conspicuously superior to those which may be obtained, for an equal concentration of sunscreen compound and in a vehicle identical in nature, employing either of the sunscreen compounds alone.

Briefly, the present invention features novel photoprotective/cosmetic compositions comprising, in a cosmetically acceptable vehicle, diluent or carrier, (i) an effective amount of 2,4,6-tris[p-((2'-ethylhexyl)oxycarbonyl)anilino]-1,3,5-triazine, as a first sunscreen compound, and (ii) an effective amount of 2-ethylhexyl α-cyano-β,β-diphenylacrylate, as a second sunscreen compound.

The present invention also features the use of such compositions as, or for the formulation of, sunscreen/cosmetic compositions intended for the photoprotection of the skin and/or the hair against ultraviolet irradiation, in particular solar radiation.

The cosmetic treatment for the photoprotection of the skin and/or the hair against ultraviolet irradiation, in particular solar radiation, comprises topically applying thereto an effective amount of a sunscreen/cosmetic composition as described above.

DETAILED DESCRIPTION OF BEST MODE AND PREFERRED EMBODIMENTS OF THE INVENTION

More particularly according to the present invention, 2,4,6-tris[p-((2'-ethylhexyl)oxycarbonyl)anilino]-1,3,5-triazine (compound A) is a sunscreen compound that is per se known to this art and is active in the UV-B range, is a solid material and is marketed under the trademark "UVINUL T 150" by BASF. This compound has the following structural formula (I):

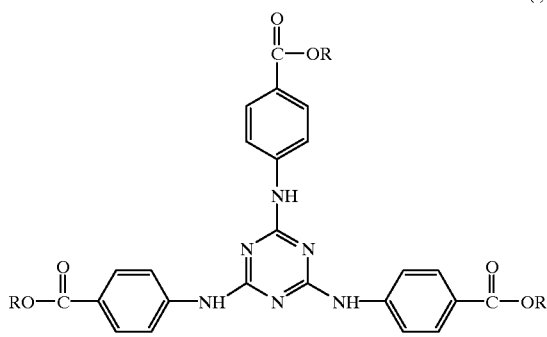

in which R is a 2-ethylhexyl radical.

Similarly, 2-ethylhexyl α-cyano-β,β-diphenylacrylate (compound B), also referred to as octocrylene, is a liquid lipophilic sunscreen compound that is also per se known to this art for its activity in the UV-B range. This too is a commercially available compound, marketed under the trademark "UVINUL N 539" by BASF. It has the following structural formula (II):

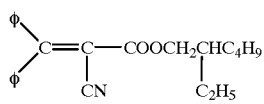

in which φ is a phenyl radical.

The compound A is advantageously present in the compositions according to the invention at a concentration ranging from 0.1% to 10% by weight, and preferably from 0.5% to 5% by weight, relative to the total weight of the composition, and compound B is advantageously present at a concentration ranging from 0.5% to 15% by weight, and preferably from 1% to 10% by weight, also relative to the total weight of the composition. The overall content of the mixture of compound A and compound B preferably does not exceed 15% of the total weight of the final composition.

From a practical standpoint, the aforesaid two compounds A and B are preferably both present in the final composition in the respective proportions such that the synergy is optimal, as regards the protection factor imparted by the resulting association. The exact range of the [compound A/compound B] weight ratios in which this optimal synergy is actually attained may vary slightly depending on the total amount of sunscreen compounds A and B used.

Moreover, the concentrations and ratios of compounds A and B are typically selected such that the sun protection factor of the final composition is preferably at least 2.

In a preferred embodiment of the present invention, the cosmetically acceptable vehicle, diluent, carrier or support in which the various compounds A and B are formulated is an emulsion of oil-in-water type.

Of course, the sunscreen/cosmetic compositions according to the invention may contain one or more additional hydrophilic or lipophilic sunscreen agents active in the UV-A and/or UV-B range (absorbers), other than the two sunscreen compounds indicated above. Exemplary of such additional sunscreens are cinnamic derivatives, salicylic derivatives, camphor derivatives, triazine derivatives, benzophenone derivatives, dibenzoylmethane derivatives, β,β-diphenylacrylate derivatives, p-aminobenzoic acid derivatives, and the sunscreen polymers and sunscreen silicones described in WO-93/04,665. Other examples of organic sunscreen agents are described in EO-A-0,487,404.

The compositions according to the invention may also contain agents for the artificial tanning and/or browning of the skin (self-tanning agents) such as, for example, dihydroxyacetone (DHA).

The cosmetic compositions according to the invention may also contain pigments or, alternatively, nanopigments (average size of the primary particles: generally ranging from 5 nm to 100 nm, preferably from 10 to 50 nm) of coated or uncoated metal oxides such as, for example, nanopigments of titanium dioxide (amorphous or crystallized in rutile and/or anatase form), of iron oxide, of zinc oxide, of zirconium oxide or of cerium oxide, which are all photoprotective agents that are per se well known to this art and which are effective by physical blocking (reflection and/or diffusion) of the UV irradiation. Conventional coating agents include, moreover, alumina and/or aluminum stearate. Such coated or uncoated metal oxide nanopigments are described, in particular, in EP-A-0,518,772 and EP-A-0,518,773.

The compositions of the invention may additionally comprise conventional cosmetic additives and adjuvants selected especially from among fats, organic solvents, ionic or nonionic thickening agents, softeners, antioxidants and especially anti-free-radical antioxidants, opacifying agents, stabilizing agents, emollients, silicones, α-hydroxy acids, antifoaming agents, hydrating agents, vitamins, fragrances, preservatives, surfactants, fillers, insect repellants, sequestering agents, polymers, propellants, basifying or acidifying agents, dyes and colorants, or any other ingredient usually employed in cosmetics, in particular for the production of sunscreen/cosmetic compositions in emulsion form.

The fats may comprise an oil or a wax or mixtures thereof, and may also comprise fatty acids, fatty alcohols and fatty acid esters. The oils may be selected from among animal, plant, mineral or synthetic oils and, especially, from among liquid petrolatum, paraffin oil, volatile or non-volatile silicone oils, isoparaffins, poly-α-olefins, fluoro oils and perfluoro oils. Similarly, the waxes may be selected from among animal, fossil, plant, mineral or synthetic waxes that are per se known to this art.

Exemplary organic solvents include the lower polyols and alcohols.

The thickening agents may be selected, especially, from among crosslinked polyacrylic acids, modified or unmodified guar gums and celluloses such as hydroxypropyl guar gum, methylhydroxyethylcellulose and hydroxypropylmethylcellulose.

The compositions of the invention may be formulated according to techniques well known to this art, in particular those intended for the preparation of emulsions of oil-in-water or water-in-oil type.

The subject compositions may, in particular, be in simple or complex (O/W, W/O, O/W/O or W/O/W) emulsion form such as a cream, a milk, a gel, an ointment or a cream gel, in powder form or in solid stick form and may optionally be packaged as an aerosol and may be provided in the form of a foam or a spray.

When it is an emulsion, the aqueous phase of this emulsion may comprise a nonionic vesicle dispersion prepared according to known processes (Bangham, Standish and Watkins, J. Mol. Biol, 13, 238 (1965), FR-2,315,991 and FR-2,416,008).

The cosmetic compositions of the invention are useful for protecting the human epidermis or the hair against the damaging effects of ultraviolet rays, as sunscreen compositions or as makeup products.

When the cosmetic compositions according to the invention are used for photoprotection of the human epidermis against UV rays, or as sunscreen compositions, they may be formulated as a suspension or a dispersion in solvents or fats, in the form of a nonionic vesicle dispersion or, alternatively, in the form of an emulsion, preferably of oil-in-water type, such as a cream or a milk, or in ointment, gel, cream gel, solid stick, stick, aerosol foam or spray form.

When the cosmetic compositions according to the invention are used for the photoprotection of the hair, they may be formulated as a shampoo, a lotion, a gel, an emulsion, a nonionic vesicle dispersion or a lacquer for the hair and may constitute, for example, a composition to be rinsed, to be applied before or after shampooing, before or after dyeing or bleaching, before, during or after permanent-waving or hair-straightening, a styling or treating lotion or gel, a blow-drying or hair-setting lotion or gel, or a composition for the permanent-waving or straightening, dyeing or bleaching of the hair.

When the subject compositions are used as a makeup product for the eyelashes, the eyebrows or the skin, such as an epidermal treatment cream, a foundation, a lipstick, an eyeshadow, a blush, a mascara or "eyeliner", they may be in anhydrous or aqueous, solid or pasty form, such as oil-in-water or water-in-oil emulsions, nonionic vesicle dispersions or, alternatively, suspensions.

For example, for the photoprotective/sunscreen formulations in accordance with this invention which comprise a vehicle of oil-in-water emulsion type, the aqueous phase (comprising hydrophilic sunscreen agents in particular) generally constitutes from 50% to 95% by weight, preferably from 70% to 90% by weight, relative to the total formulation, the oily phase (comprising lipophilic sunscreen agents in particular) from 5% to 50% by weight, preferably from 10% to 30% by weight, relative to the total formulation, and the (co)emulsifying agent(s) from 0.5% to 20% by weight, preferably from 2% to 10% by weight, relative to the total formulation.

The cosmetic treatment of the skin or hair to protect same against the deleterious effects of UV rays, especially those contained in solar radiation, comprises applying thereto an effective amount of a sunscreen/cosmetic composition as described above.

In order to further illustrate the present invention and the advantages thereof, the following specific examples are given, it being understood that same are intended only as illustrative and in nowise limitative.

EXAMPLE 1

Various photoprotective/sunscreen formulations in the form of an emulsion of oil-in-water type were prepared, containing (the amounts are expressed as % by weight relative to the total weight of the composition):

| | |
|---|---|
| (a) A first sunscreen agent A, i.e., 2,4,6-tris[p-((2'-ethylhexyl)oxycarbonyl)anilino]1,3,5-triazine ("UVINUL T150"), in an amount of | x% |
| (b) A second sunscreen agent B, i.e., 2-ethylhexyl α-cyano-β,β-diphenylacrylate ("UVINUL N 539"), in an amount of | y% |
| (c) Diisopropyl adipate (fat) | 15% or 20% |
| (d) Crosslinked terpolymer: methacrylic acid/ethyl acrylate/steareth-10 allyl ether, as a 30% aqueous emulsion ("SALCARE SC 90" marketed by Allied Colloids) (emulsifying agent) | 5% |
| (e) Triethanolamine | 0.75% |
| (f) Preservatives | qs |
| (h) Water | qs 100% |

These formulations (numbered 1 and 2 for those in accordance with the invention) had various y/x weight ratios between the sunscreen agents B and A. Comparative formulations were also prepared corresponding to each of these formulations, the comparative formulations either containing only the sunscreen agent A at the weight concentration x, or containing only the sunscreen agent B at the weight concentration y. The formulations 1, 1A and 1B contained 20% of fat, and the formulations 2, 2A and 2B only 15% of fat.

Each of the above emulsions was prepared by dissolving the sunscreen agents into the fatty phase and then adding the emulsifying agents into this fatty phase, heated to about 80° C., and, lastly, adding, with rapid stirring, the aqueous phase which had been preheated to this same temperature.

For each of the formulations thus prepared, the sun protection factor (SPF) associated therewith was then determined. The SPF was determined using the in vitro method described by B. L. Diffey et al, in *J. Soc. Cosmet. Chem.*, 40, 127–133 (1989); this technique entailed determining the monochromatic protection factors every 5 nm over a range of wavelengths from 290 to 400 nm and in calculating, from the latter, the sun protection factor according to a given mathematical equation.

The compositions of the various formulations examined and the results obtained, as a mean protection factor, are reported in the Table below:

TABLE

| Sunscreen | Formulations | | | | | |
|---|---|---|---|---|---|---|
| Agents | 1 | 1A | 1B | 2 | 2A | 2B |
| A (x%) | 10 | 10 | — | 5 | 5 | — |
| B (y%) | 10 | — | 10 | 15 | — | 15 |
| A + B (x + y%) | 20 | 10 | 10 | 20 | 5 | 15 |
| y/x Weight ratio | 1 | — | — | 3 | — | — |
| Average SPF (standard deviation) | 7.5 (1.2) | 2.8 (0.1) | 2.3 (0.2) | 7.3 (0.2) | 1.8 (0.1) | 3.1 (0.3) |

These results clearly demonstrate the synergistic effect obtained with compositions 1 and 2 in accordance with the invention, the sun protection factors attributed to these compositions being notably and significantly higher in all instances than the simple arithmetic sum of the sun protection factors of the corresponding comparative compositions containing only one sunscreen agent.

EXAMPLE 2

Another specific example of a photoprotective/sunscreen composition in accordance with the invention, in the form of an emulsion of oil-in-water type, is as follows:

| | |
|---|---|
| (a) 2,4,6-Tris[p-((2'-ethylhexyl)oxycarbonyl)anilino]-1,3,5-triazine ("UVINUL T150") | 4 g |
| (b) 2-Ethylhexyl α-cyano-β,β-diphenylacrylate ("UVINUL N 539") | 10 g |
| (c) 2-Ethylhexyl p-methoxycinnamate ("PARSOL MCX" marketed by Givaudan) (sunscreen) | 1 g |
| (d) Mixture of cetylstearyl alcohol and oxyethylenated cetylstearyl alcohol containing 33 moles of ethylene oxide ("SINNOWAX AO" marketed by Henkel) (emulsifying agent) | 7 g |
| (e) Mixture of glyceryl mono-, di- and tristearate (coemulsifying agent) | 2 g |

-continued

| | |
|---|---|
| (f) Diisopropyl adipate | 15 g |
| (g) Polydimethylsiloxane | 1.5 g |
| (h) Cetyl alcohol | 1.5 g |
| (i) Preservatives | qs |
| (j) Distilled water | qs 100 g |

This emulsion was prepared as in Example 1.

EXAMPLE 3

Yet another specific example of a photoprotective/sunscreen composition in accordance with the invention, in this instance in the form of an emulsion of water-in-oil type, is as follows:

| | |
|---|---|
| (a) 2,4,6-Tris[p-((2'-ethylhexyl)oxycarbonyl)-anilino]-1,3,5-triazine ("UVINUL T150") | 1 g |
| (b) 2-Ethylhexyl α-cyano-β,β-diphenylacrylate ("UVINUL N 539") | 5 g |
| (c) [Glyceryl and sorbitol hydroxystearate and isostearate] mixture containing 20 moles of propylene oxide and 30 moles of ethylene oxide ("ARLACEL 780" marketed by ICI) | 2.5 g |
| (d) NaCl | 0.7 g |
| (e) Liquid petrolatum | 20 g |
| (f) Preservatives | qs |
| (g) Fragrance | qs |
| (h) Water | qs 100 g |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable sunscreen/cosmetic composition adopted for the photoprotection of human skin and/or hair, comprising a photoprotecting synergistically effective amount of (i) 2,4,6-tris[p-((2'-ethylhexyl)oxycarbonyl) anilino]-1,3,5-triazine and (ii) 2-ethylhexyl α-cyano-β,β-diphenylacrylate, in a cosmetically acceptable vehicle, diluent or carrier therefor.

2. The sunscreen/cosmetic composition as defined by claim 1, comprising from 0.1% to 10% by weight of said triazine compound (i).

3. The sunscreen/cosmetic composition as defined by claim 2, comprising from 0.5% to 5% by weight of said triazine compound (i).

4. The sunscreen/cosmetic composition as defined by claim 2, comprising from 0.5% to 15% by weight of said diphenylacrylate compound (ii).

5. The sunscreen/cosmetic composition as defined by claim 3, comprising from 1% to 10% by weight of said diphenylacrylate compound (ii).

6. The sunscreen/cosmetic composition as defined by claim 1, comprising an oil-in-water emulsion.

7. The sunscreen/cosmetic composition as defined by claim 1, comprising a water-in-oil emulsion.

8. The sunscreen/cosmetic composition as defined by claim 1, further comprising at least one additional hydrophilic or lipophilic organic UV-A and/or UV-B sunscreen.

9. The sunscreen/cosmetic composition as defined by claim 8, further comprising at least one cinnamic derivative, salicylic derivative, camphor derivative, triazine derivative, benzophenone derivative, dibenzoylmethane derivative, β,β-diphenylacrylate derivative, p-aminobenzoic acid derivative, sunscreen polymer, or sunscreen silicone.

10. The sunscreen/cosmetic composition as defined by claim 1, further comprising a photoprotecting effective amount of particulates of at least one inorganic pigment or nanopigment.

11. The sunscreen/cosmetic composition as defined by claim 10, said at least one pigment or nanopigment comprising titanium dioxide, zinc oxide, iron oxide, zirconium oxide, cerium oxide, or mixture thereof.

12. The sunscreen/cosmetic composition as defined by claim 1, further comprising at least one active agent for the artificial tanning and/or browning of human skin.

13. The sunscreen/cosmetic composition as defined by claim 1, further comprising at least one cosmetically acceptable adjuvant or additive.

14. The sunscreen/cosmetic composition as defined by claim 13, said at least one adjuvant or additive comprising a fat, organic solvent, ionic or nonionic thickening agent, softener, antioxidant, anti-free-radical antioxidant, opacifying agent, stabilizing agent, emollient, silicone, α-hydroxy acid, anti-foaming agent, hydrating agent, vitamin, fragrance, preservative, surfactant, filler, sequestering agent, polymer, propellant, insect repellent, basifying or acidifying agent, dye, colorant, or mixture thereof.

15. The sunscreen/cosmetic composition as defined by claim 1, comprising a nonionic vesicle dispersion, emulsion, cream, milk, gel, cream gel, ointment, suspension, dispersion, powder, solid stick, foam or spray.

16. The sunscreen/cosmetic composition as defined by claim 1, comprising a makeup.

17. The sunscreen/cosmetic composition as defined by claim 16, comprising an anhydrous or aqueous solid or paste, emulsion, suspension, or dispersion.

18. The sunscreen/cosmetic composition as defined by claim 1, comprising a shampoo, lotion, gel, emulsion, nonionic vesicle dispersion, hair lacquer, or rinse.

19. The sunscreen/cosmetic composition as defined by claim 1, having a sun protection factor of at least 2.

20. A method for protecting human skin and/or hair against the deleterious effects of ultraviolet irradiation, comprising topically applying thereto an effective amount of the sunscreen/cosmetic composition as defined by claim 1.

21. A method for protecting human skin and/or hair against the deleterious effects of solar radiation, comprising topically applying thereto an effective amount of the sunscreen/cosmetic composition as defined by claim 1.

* * * * *